(12) United States Patent
Smith et al.

(10) Patent No.: US 7,799,083 B2
(45) Date of Patent: Sep. 21, 2010

(54) PROSTHESIS FOR RESTORING MOTION IN AN APPENDAGE OR SPINAL JOINT AND AN INTERVERTEBRAL SPACER

(75) Inventors: Colin M. Smith, Dana Point, CA (US); Nicholas M. Cordaro, Vista, CA (US)

(73) Assignee: Seaspine, Inc., Vista, CA (US)

(*) Notice: Subject to any disclaimer, the term of this patent is extended or adjusted under 35 U.S.C. 154(b) by 276 days.

(21) Appl. No.: 11/919,615

(22) PCT Filed: Apr. 28, 2006

(86) PCT No.: PCT/US2006/016392

§ 371 (c)(1),
(2), (4) Date: Oct. 30, 2007

(87) PCT Pub. No.: WO2006/119088

PCT Pub. Date: Nov. 9, 2006

(65) Prior Publication Data

US 2009/0082868 A1    Mar. 26, 2009

Related U.S. Application Data

(60) Provisional application No. 60/676,744, filed on May 2, 2005.

(51) Int. Cl.
*A61F 2/44* (2006.01)
(52) U.S. Cl. .................................. 623/17.16
(58) Field of Classification Search ... 623/17.11–17.16; 606/246, 249
See application file for complete search history.

(56) References Cited

U.S. PATENT DOCUMENTS

| | | | |
|---|---|---|---|
| 4,871,366 A * | 10/1989 | von Recum et al. ...... 623/23.74 |
| 5,071,437 A | 12/1991 | Steffee |
| 5,425,773 A | 6/1995 | Boyd et al. |
| 5,676,701 A | 10/1997 | Yuan |
| 5,755,796 A | 5/1998 | Ibo et al. |
| 5,899,941 A | 5/1999 | Nishijima et al. |
| 6,113,637 A | 9/2000 | Gill et al. |
| 6,113,638 A * | 9/2000 | Williams et al. ............ 128/898 |
| 6,206,924 B1 * | 3/2001 | Timm ...................... 623/17.16 |
| 6,368,350 B1 * | 4/2002 | Erickson et al. .......... 623/17.14 |
| 6,368,354 B2 | 4/2002 | Burstein et al. |

(Continued)

FOREIGN PATENT DOCUMENTS

DE        2263842        12/1972

OTHER PUBLICATIONS

Hoffman-Daimler, Intervertebral Disk Displacement, vol. 112, No. 4, Aug. 1974.

(Continued)

*Primary Examiner*—Alvin J. Stewart (57) ABSTRACT

A motion restoring prosthesis to be interposed between the ends of two bones adjoining a mammalian appendage or spinal joint is formed of two components with the components having inner cooperating articulating surfaces and outer bone engaging surfaces. At least one of the components has an inner section made of relatively hard, stiff material defining one or the articulating surfaces and an outer section made of a softer material defining the bone engaging surface. The softer material having a hardness/stiffness characteristic compatible with the bone to reduce stress shielding and more evenly distribute the forces from the articulating surfaces to the associate bone interface.

20 Claims, 8 Drawing Sheets

U.S. PATENT DOCUMENTS

| | | | |
|---|---|---|---|
| 6,572,619 B2 * | 6/2003 | Santilli | 623/17.11 |
| 6,595,998 B2 * | 7/2003 | Johnson et al. | 606/90 |
| 6,673,075 B2 * | 1/2004 | Santilli | 623/17.16 |
| 6,699,288 B2 * | 3/2004 | Moret | 623/17.16 |
| 6,706,068 B2 | 3/2004 | Ferree | |
| 6,736,849 B2 * | 5/2004 | Li et al. | 623/17.11 |
| 6,743,257 B2 * | 6/2004 | Castro | 623/17.16 |
| 6,758,862 B2 * | 7/2004 | Berry et al. | 623/17.16 |
| 6,793,678 B2 * | 9/2004 | Hawkins | 623/17.15 |
| 6,800,092 B1 * | 10/2004 | Williams et al. | 623/17.11 |
| 6,802,863 B2 | 10/2004 | Lawson et al. | |
| 6,805,714 B2 * | 10/2004 | Sutcliffe | 623/17.11 |
| 6,805,898 B1 * | 10/2004 | Wu et al. | 427/2.25 |
| 6,899,735 B2 * | 5/2005 | Coates et al. | 623/17.16 |
| 6,964,686 B2 | 11/2005 | Gordon | |
| 6,966,929 B2 * | 11/2005 | Mitchell | 623/17.11 |
| 6,966,932 B1 | 11/2005 | Schroeder | |
| 7,048,764 B2 | 5/2006 | Ferree | |
| 7,156,876 B2 * | 1/2007 | Moumene et al. | 623/17.13 |
| 7,198,643 B2 | 4/2007 | Zubok et al. | |
| 7,217,293 B2 * | 5/2007 | Branch, Jr. | 623/17.16 |
| 7,235,101 B2 * | 6/2007 | Berry et al. | 623/17.11 |
| 7,250,060 B2 * | 7/2007 | Trieu | 623/17.15 |
| 7,276,082 B2 | 10/2007 | Zdeblick et al. | |
| 7,331,994 B2 | 2/2008 | Gordon et al. | |
| RE40,260 E | 4/2008 | Bühler | |
| 7,494,507 B2 | 2/2009 | Dixon et al. | |
| 7,494,508 B2 | 2/2009 | Zeegers | |
| 7,517,363 B2 * | 4/2009 | Rogers et al. | 623/17.11 |
| 7,537,612 B2 * | 5/2009 | Kunzler | 623/17.13 |
| 7,563,284 B2 * | 7/2009 | Coppes et al. | 623/17.12 |
| 2003/0045939 A1 | 3/2003 | Casutt | |
| 2004/0243241 A1 | 12/2004 | Istephanous et al. | |
| 2005/0038516 A1 | 2/2005 | Spoonamore | |
| 2005/0055098 A1 | 3/2005 | Zdeblick et al. | |
| 2005/0154462 A1 | 7/2005 | Zucherman et al. | |
| 2005/0159818 A1 | 7/2005 | Blain | |
| 2005/0197706 A1 | 9/2005 | Hovorka et al. | |
| 2005/0283242 A1 | 12/2005 | Zucherman et al. | |
| 2006/0116769 A1 | 6/2006 | Marnay et al. | |
| 2006/0136061 A1 | 6/2006 | Navarro et al. | |
| 2006/0229729 A1 | 10/2006 | Gordon et al. | |
| 2009/0210060 A1 | 8/2009 | de Villiers et al. | |

OTHER PUBLICATIONS

Trouillier, H. et al., "Report on Two Failed Posterior Lumbar Interbody Fusions", SICOT Online Report E034: Accepted May 6, 2003, Department of Orthopedic Surgery, Institute of Pathology, Ludwig-Maximilians University, Munich, Germany, pp. 1-12.

Final Office Action from U.S. Appl. No. 11/919,616, dated Jul. 8, 2010, 11 pages.

* cited by examiner

PROSTHESIS FOR RESTORING MOTION IN AN APPENDAGE OR SPINAL JOINT AND AN INTERVERTEBRAL SPACER

RELATED APPLICATION

This application is based on and claims priority of U.S. Provisional Application No. 60/676,744 ("'744 application") for a Motion Restoring Intervertebral Device filed on May 2, 2005, the contents of the provisional application are incorporated herein by reference.

FIELD OF THE INVENTION

This application relates to (a) motion restoring prosthesis for placement between the ends of two bones adjoining a mammalian appendage or spinal joint, such as an artificial intervertebral disc or hip/knee/shoulder joint and (b) intervertebral spacer for accommodating fusion between the separated vertebrae.

BACKGROUND OF THE INVENTION

With respect to motion restoring intervertebral devices see German Patent No. 2,263,842 and the devices disclosed therein. These include ball and socket prostheses with single and/or dual articulations and with and without motion dampening elements. The clinical use of the device containing a ball supported by two opposing sockets extending from generally flat plates, was discussed in a Hoffmann-Daimler's article appearing in Intervertebral Disk Displacement, Vol. 112, No. 4, Aug. 1974. Hansen et al., U.S. Pat. No. 5,676,701 ("'701 patent") discloses a low wear artificial spinal disc having opposing convex and concave contoured surfaces with a full 360 degree circumference. This allows for rotation but no translation. Yuichiro and Koichi, U.S. Pat. No. 5,899,941 discloses a similar device, but where the articulating surface is generally non-conforming to allow rotation and translational movement. This is similar to the device illustrated in U.S. Pat. No. 6,113,637 by Gill et al. This artificial spinal disc incorporates a ball and trough type articulation with a substantially flat portion. Both the Yuichiro and Gill et al. patents describe devices which rely on point contact, a potential source of excessive wear debris.

Also, see the prior art discussed in the '701 patent and U.S. Pat. No. 5,071,437 ("'437 patent"). These prior art intervertebral devices generally rely on an elastomeric core to provide the articulation, which core is sandwiched between rigid plates abutting the respective vertebral bodies ("'437 patent") or hard metal ball and socket components interposed between adjacent vertebrae.

The use of a hard/stiff material, generally ceramic or a cobalt chromium alloy, to provide the articulating surfaces decreases the wear and increases the life expectancy of the artificial disc. However, the use of the same material or rigid plates, as in the '437 patent, abutting the faces of the separated vertebrae, results in stress shielding, i.e., a nonuniform distribution of the forces transmitted from the articulating surfaces to the abutted vertebrae bone faces. This nonuniform loading can result in so called hard spots on the bone face where the load is being transmitted and soft spots where little or no load is being transmitted, with the consequence that the soft spots tend to result in bone absorption, thereby loosening the implant and causing eventual failure.

There is a need to provide a softer/less stiff material to interface with the vertebrae bone faces and a hard material to serve as the articulating surfaces. Since a softer material, capable of supporting the articulating layer, may not be conducive for bone attachment, there is a need to modify the vertebrae engaging or buttressing surface of the softer material to facilitate bone attachment. There is a further need to inhibit any slight motion, e.g., macromotion, between the material forming the articulation surface and the material forming the vertebrae engaging or bone buttressing surface to reduce or eliminate any wear at the interface of these materials. Such wear, given time, will cause separation at the interface and shorten the useful life of the prosthesis.

The above problems are also associated with artificial limb replacement joints, except that some joint replacements such as hip joints may, as a practical matter, have a need to relieve the stress imparted only to one of the bone ends, e.g., the bone portion forming the acetabulum. Artificial hip joints typically include a metal cup which houses the acetabular bearing portion, which metal cup is secured, via cement, for example, directly to the bone. See, for example, U.S. Pat. Nos. 6,368,354 ("'354 patent") and 6,966,932 ("'932 patent"). As discussed above, the metal to bone contact provides a nonuniform stress loading to the exposed bone face with a significant potential of causing the implant to loosen from the underlying implant. It is noted that both of the above patents illustrate an interlocking arrangement between several sections of the acetabular component. However, the interface between the outer metal shell and the bone end or face forming the acetabulum does not resolve the nonuniform loading on the bone face. As with the artificial intervertebral joint there is a need to provide stress shielding in artificial hip replacements as well as in other artificial appendage joints.

With respect to item (b) above, a spacer or disc replacement member, made of a material such as Ti, has been used to maintain the vertebrae encompassing a failed natural disc in a separated condition during the fusion process. Currently, spacers formed of a softer material, such as PEEK, have been used for this purpose to provide better stress transfer to the bone during the fusion process. However, PEEK is not particularly bone attachment friendly. There is a need to provide an artificial disc replacement member which accommodates both even stress transfer and bone-on growth attachment.

SUMMARY OF THE INVENTION

In a broad sense a motion restoring prosthesis adapted to be placed between the ends of two bones adjoining a mammalian appendage or spinal joint, in accordance with the present invention, includes two components with each component defining an outer surface for attachment to a respective bone end and an articulating surface for engaging the articulating surface of the other component. At least one of the components has an inner and outer section. The inner section, defining the articulating surface, is made of a primary relatively hard/stiff material such as ceramic, cobalt chromium, or other hard, stiff bio-compatible material for inhibiting the wear between the articulating surfaces. The outer section is made of a secondary material (sometimes hereinafter referred to as the "bone buttressing material") that is softer and less stiff than the primary material (sometimes referred to as the "articulating material"). Preferably the secondary material is formed of a biocompatible polymer having a hardness/stiffness characteristic closer to that of the bone to be buttressed. Polyetheretherketone ("PEEK") or carbon fiber reinforced PEEK ("CFRPEEK") are clear choices. These polymers reduce stress shielding by more evenly distributing the forces or load from the articulating surfaces to the respective bone interface end thereby enhance the life of the prosthesis.

Preferably the flexural moduli of the primary and secondary materials are, respectfully, within the range of about 80± and about 60 or less on the Giga Pascal Scale (GPa), which scale provides a measure of elasticity versus pressure. Most preferably the secondary material has a GPa range of about 4 to 30 or about 12-25 while cortical bone has a GPa of about 17±5-8.

Optionally, the bone buttressing surface of each of the outer sections are roughened and/or made uneven to enhance the attachment of bone thereto. Further, it is desirable for the bone buttressing surface to have a very thin coating or layer of a bone-on growth attachment friendly material, such as titanium, calcium phosphate or hydroxyapatite thereon, which does not materially increase the stiffness of the bone buttressing surface of the secondary material to detract from the stress shielding characteristic thereof, while enhancing the attachment of the bone thereto. Preferably the thin coating of such material is within the range of about 0.5 to 15.0 or more microns and most preferably within the range of about 0.50 to 3.0 microns.

In a narrower sense, and particularly for creating artificial spinal joints, both components are formed with inner and outer sections. The inner sections are formed of the primary material and preferably define a ball and socket type articulating surface as described in the '744 application. The outer sections are formed of the softer secondary material which define the bone buttressing surfaces for attachment to the respective bone faces of the separated vertebral bodies.

Again, it is preferable that the softer outer sections partially encapsulate the inner sections, e.g., by an injection molding process, to substantially prevent any motion including macromotion between the inner and outer sections.

With respect to item (b) an artificial intervertebral disc or spacer, for accommodating fusion, is preferably formed of a material such as PEEK or CRFPEEK having a flexure modulus comparable to that of cortical bone. The spacer is provided with a roughened and/or uneven surface and subsequently provided with a very thin coating of a material such as Ti which enhances bone-on growth without adversely affecting the bone friendly surface characteristic of the PEEK or CFRPEEK as discussed above.

The invention may best be understood in reference to the following description taken in conjunction with the appended drawings where like components and parts thereof are given the same or primed numerals in the several figures.

DESCRIPTION OF THE PREFERRED EMBODIMENTS

Figure 1:
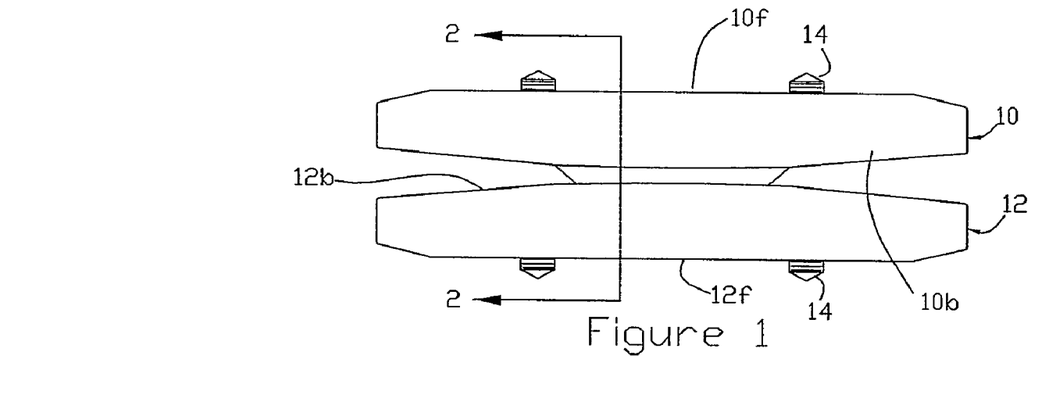
FIG. 1 is a side elevational view of a motion restoring prosthesis for replacing a natural spinal disc in accordance with the present invention.
Figure 2:
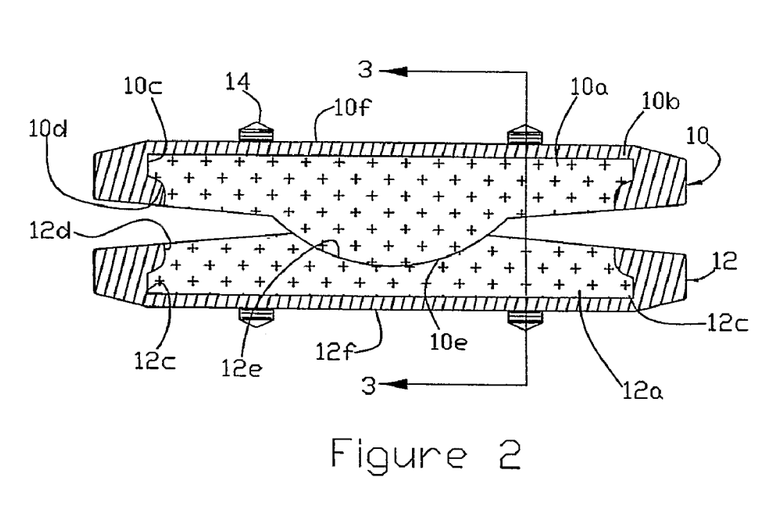
FIG. 2 is a cross-sectional view of the prosthesis of FIG. 1 taken along lines 2-2 of FIG. 1.
Figure 3:
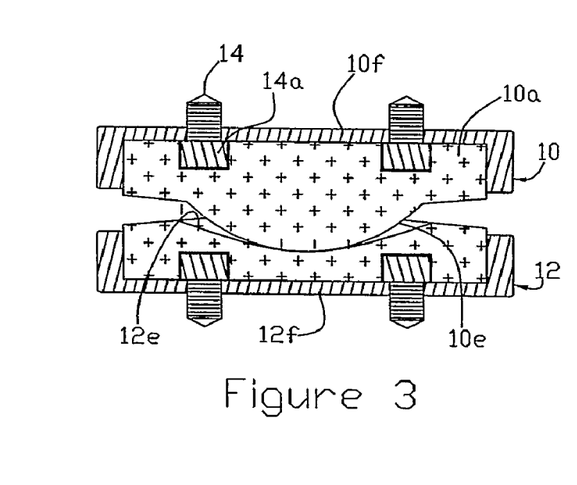
FIG. 3 is a cross-sectional view of the prosthesis of FIG. 1 taken along lines 3-3 of FIG. 2.

Referring now to FIGS. 1-3, a motion restoring intervertebral prosthesis, in accordance with this invention, comprises first and second components 10 and 12 with the components having inner sections 10a and 12a (formed of a primary material) and outer sections 10b and 12b (formed of a secondary material), respectively. The sections are integrally formed, preferably by an injection molding process, so that the secondary material partially encloses or encapsulates the primary material (except for the articulating surfaces) as will be explained with respect to FIG. 17. Briefly, outwardly extending protrusions 10c and 12c of the primary material are overlapped by an inwardly extending shoulders 10d and 12d of the secondary material. The inner sections 10a and 12a define cooperating articulating surfaces 10e and 12e in the form of a ball and modified socket to provide controlled rotation in the frontal plane and controlled rotation with translation in the sagittal plane as is described in some detail in the '744 application (and in the companion PCT application no. PCT/US06/16392 based on the provisional application and filed herewith) in connection with FIGS. 3 and 4. The top outer surfaces 10f and 12f form the bone (vertebral) buttressing surfaces.

The primary material is formed from a relatively hard, stiff material, such ceramic or a cobalt chromium alloy, to minimize the wear between the articulating surfaces and increase the life expectancy of the prosthesis.

The secondary or bone buttressing material is softer and less stiff than the primary material to accommodate surface irregularities in the underlying vertebral bone faces and more evenly distribute the forces or load from the articulating surfaces to the respective bone faces thereby inhibiting the formation of the hot and cold spots. In this manner it is believed that the softer secondary material serves to dampen the stresses imparted to the bone faces and increase the life expectancy of the prosthesis.

The secondary material should have a flexural modulus on the GPa scale of about 60 or less and preferably within the range of 4 to 30 and most preferably about 17±5-8 which is the flexural modulus spectrum of cortical bone. The primary material may be made of a bio-compatible ceramic, e.g., alumina ceramic, which has a GPa flexural modulus of about 158±10% while another suitable primary materials is cobalt chromium alloy (including some molybdenum) which has GPa flexural modulus of about 80.

PEEK is an excellent implantable bio-compatible material suitable for use as the secondary material with a GPa flexural modulus of about 4 and when reinforced with 20% carbon fiber has a GPa of about 18. The carbon fiber content may be adjusted from 0 to about 80%, but we have found that a mixture of about 30 to 35% of carbon fiber by weight provides a preferred bone-to-implant surface while providing sufficient support for the molded insert of articulating (primary) material and it has a stiffness slightly higher than the average (i.e., about 17 GPa) for cortical bone, but less than 30 GPa, i.e, about 21-24, while being imaging friendly, i.e., translucent to the conventional imaging processes. Protrusions 14, commonly referred to as keels, may be in the form of headed rods or bolts for enhancing the attachment of the prosthesis to the underlying bone. The heads 14a of the rods are preferably embedded in the inner sections as shown.

Figure 4:
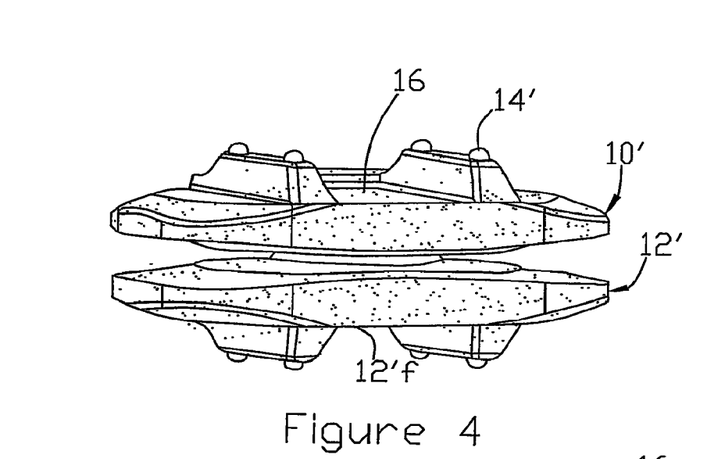
FIGS. 4 and 5 are perspective and cross-sectional views, respectfully, of a slightly modified artificial spinal disc in which the bone buttressing surface of the secondary material are coated with a coating of bone-on growth attachment friendly material.
Figure 5:
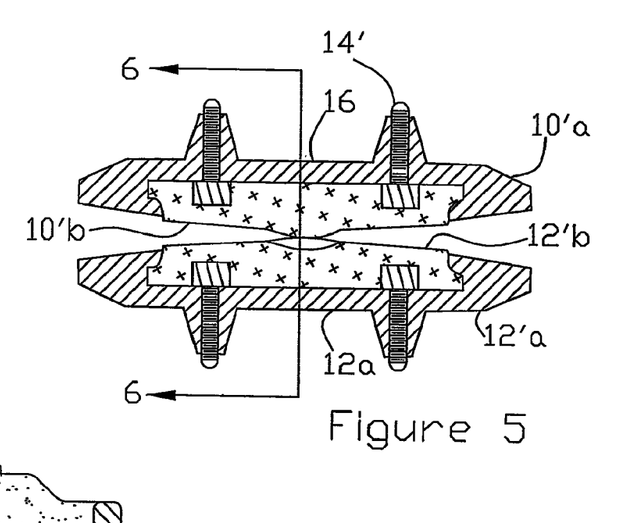
Figure 6:
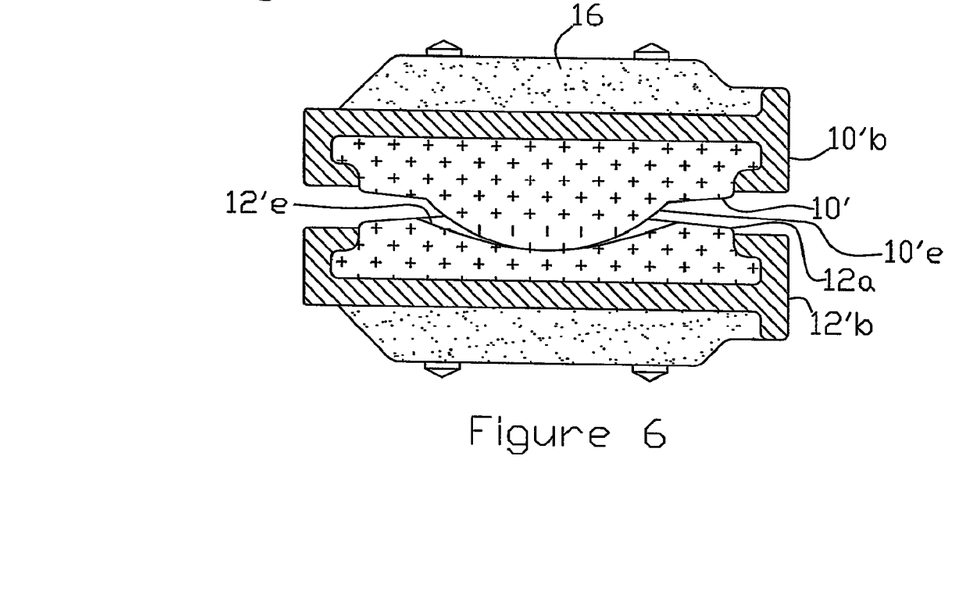
FIG. 6 is a cross-sectional view taken along lines 6-6 of FIG. 5.

FIGS. 4, 5, and 6 illustrate a slightly different design of a motion restoring vertebral prosthesis, with primed numerals being used to refer to corresponding components and portions of the prosthesis of FIGS. 1-3. In this embodiment the outer surfaces of the second components, formed of the secondary material, are coated with a very thin layer 16 of a material which promotes the affixation of bone to the bone buttressing surfaces while essentially maintaining the ability of such surfaces to accommodate surface irregularities of the bone face and provide stress softening. We have found that a very thin coating of Ti, calcium phosphate or hydroxyapatite serves this purpose. Such coating or layer can be applied by a conventional vacuum/electronic ionic fusion processes. As pointed out earlier, such a coating should have a thickness within the range of about 0.5 to 15.0 microns and most preferably between about 0.5 to 3.0 microns. It should be noted that such a coating on a prosthesis component made of the described secondary material forming a bone buttressing surface may be useful independently of the material forming the articulating surface.

Figure 7:
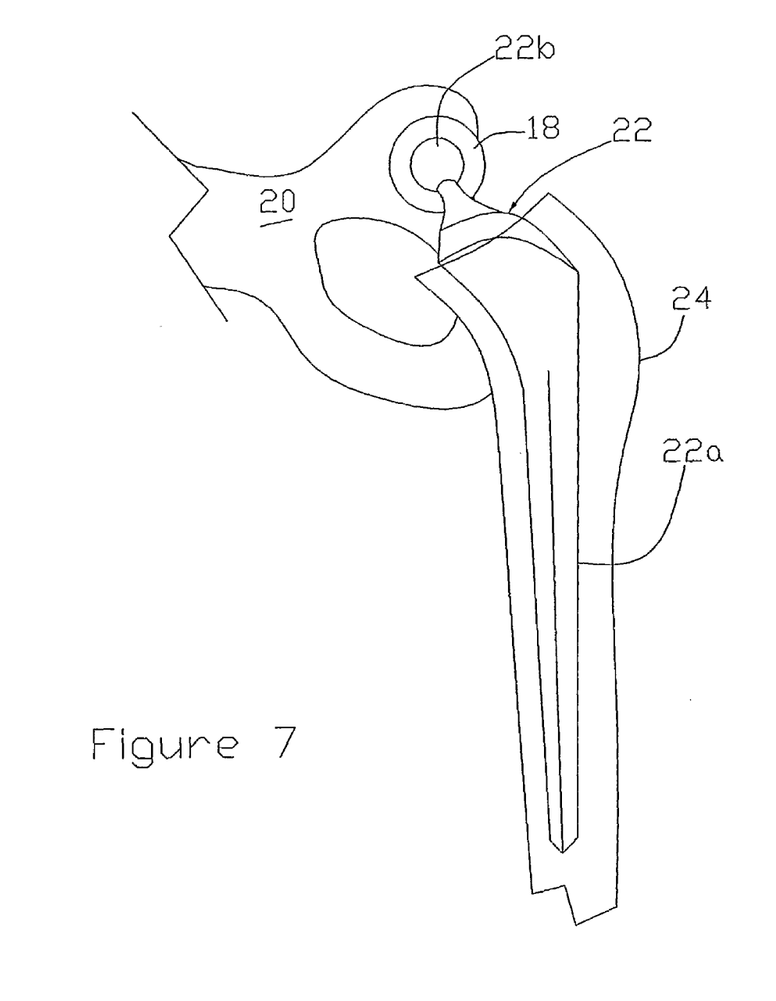
FIG. 7 is a simple diagrammatic view of a hip joint prosthesis illustrating a dual section acetabular component in accordance with this invention.
Figures 8, 9:
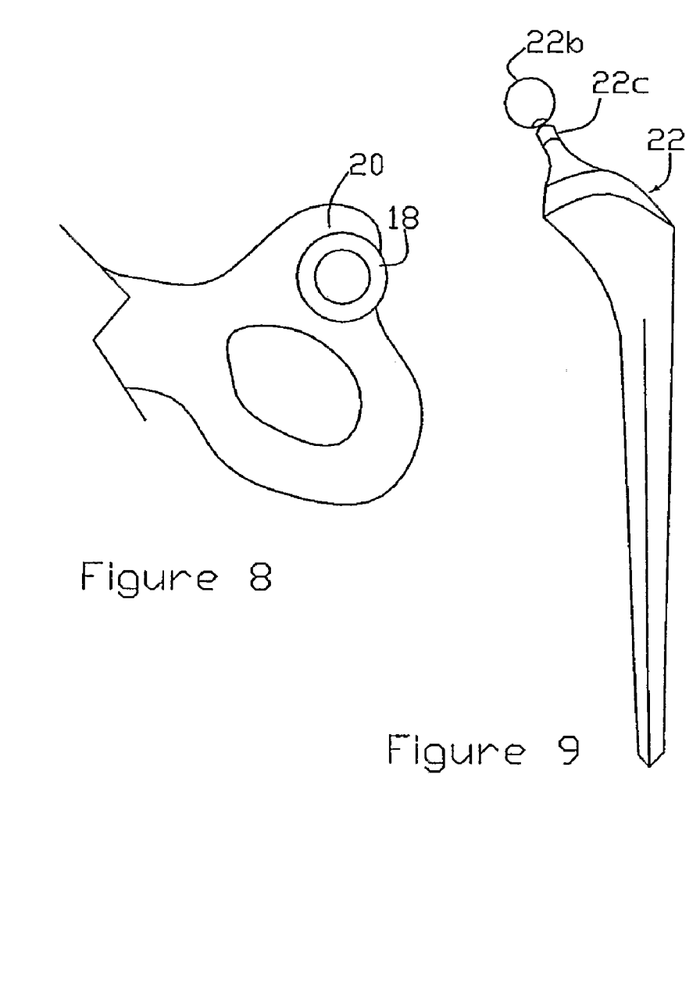
FIGS. 8, 9, and 10 are simple diagrammatic views showing the several parts which make up the prosthesis of FIG. 7 in a partially unassembled and assembled condition.
Figure 10:
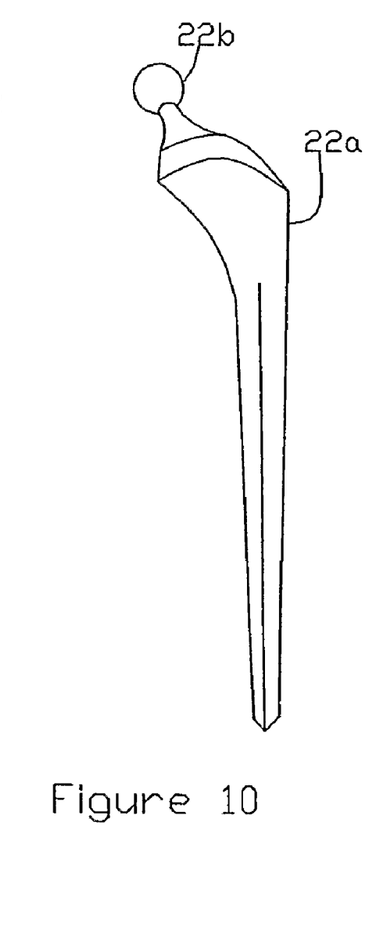
Figure 11:
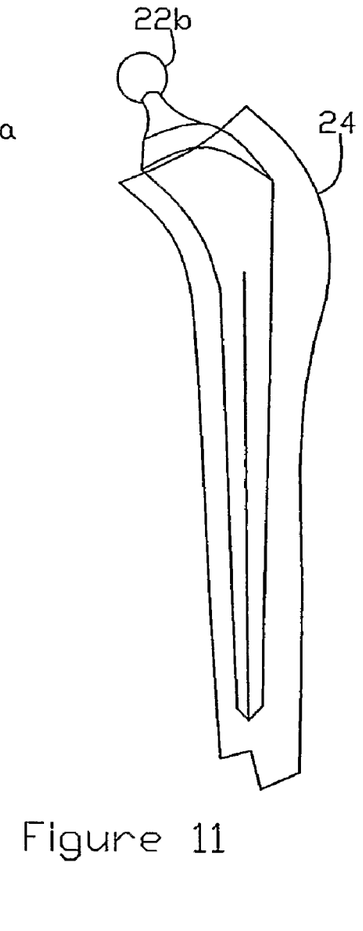
FIG. 11 is a diagrammatic view of the femoral component inserted in the femoral bone.
Figure 12:
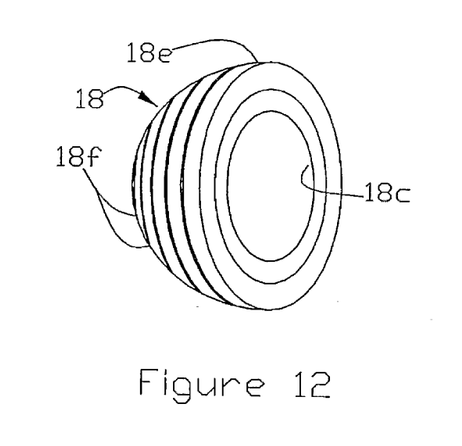
FIGS. 12, 13, and 14 are perspective, front and rear elevational views, respectively, of an acetabular component of the hip joint prosthesis of FIG. 7.
Figure 13:
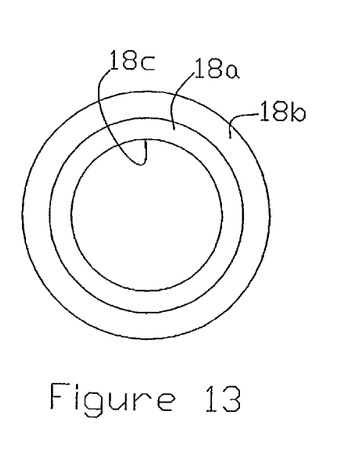
Figure 14:
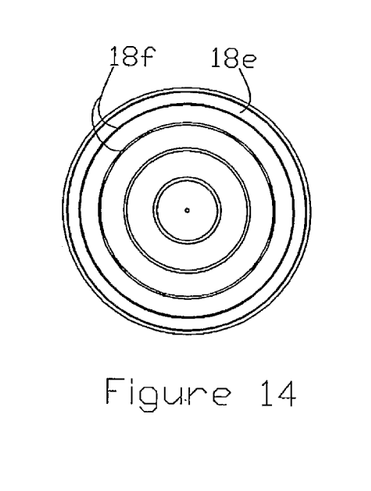
Figure 15:
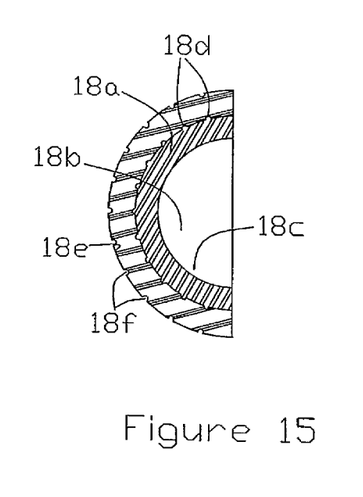
FIG. 15 is a cross-sectional view of the acetabular component of FIGS. 11-13 showing the inner and outer cup sections.
Figure 16:
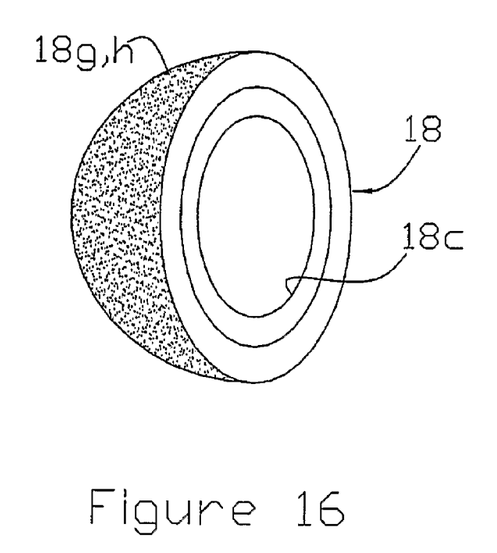
FIGS. 16 and 17 are cross-sectional and perspective views of an acetabular cup showing an outside uneven and roughened surface with a thin layer of coating of a bone-on growth friendly attachment material thereon.

A hip joint prosthesis is illustrated in FIGS. 8-16. With this type of prosthesis it is feasible, as a general rule, to form only the acetabular component 18 with a relatively soft outer secondary bone buttressing material, such as PEEK or CFRPEEK, secured over the harder and stiffer inner primary articulating material such as ceramic. FIG. 7, in diagrammatic format, illustrates a completed hip joint prosthesis in which an acetabular component 18 is fixed to the underlying acetabulum 20. A femoral component 22 comprises a conventional rod 22a inserted into the patient's femur 24 with the end of the rod carrying a conventional ball 22b of primary material positioned on a shaft 22c. FIGS. 8-11 illustrate the components in an unassembled and partially assembled form.

Figure 17:
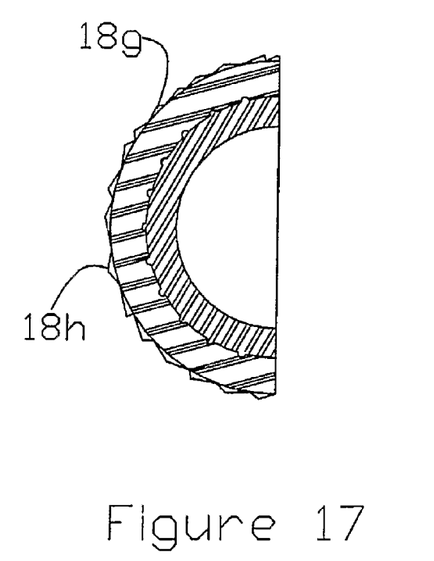
Figure 18:
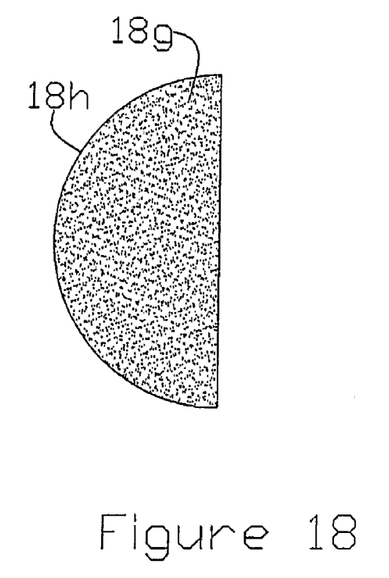
FIG. 18 is a side elevational view of the acetabular component of FIG. 15.

The present invention, with respect to this type of prosthesis, concerns the structure of the acetabular component 18, which, as is illustrated in FIGS. 12-15, comprises an inner section 18a and an outer section 18b. Section 18a, like section 10a of the first component of the device of FIGS. 1-3, is formed of a relatively hard/stiff material such as ceramic to form an inner semi-spherical articulating surface 18c for cooperating with the femoral ball 22b. The inner section 18a is mounted within the outer section 18b, preferably via an injection molding process in which tongues and grooves 18d are preferably formed in the outer surface of the first component prior to the molding step to mechanically lock the first and second components together. The outer or bone buttressing surface 18e of the second semi-spherical section 18b is preferably formed in the mold with (circular) grooves 18f (forming an uneven surface) to aid in locking the bone buttressing surface to the bone. Alternatively (and additionally) the bone buttressing surface may be roughened by blasting the surface with an appropriate abrasive resorbable media, such as kieserite after the molding step to provide a roughened surface 18g, as is illustrated in FIGS. 17 and 18. This roughened and/or uneven surface is then preferably provided with a thin micron layer 18h bone-on growth attachment enhancing material such as Ti. See FIG. 18.

Figure 19:
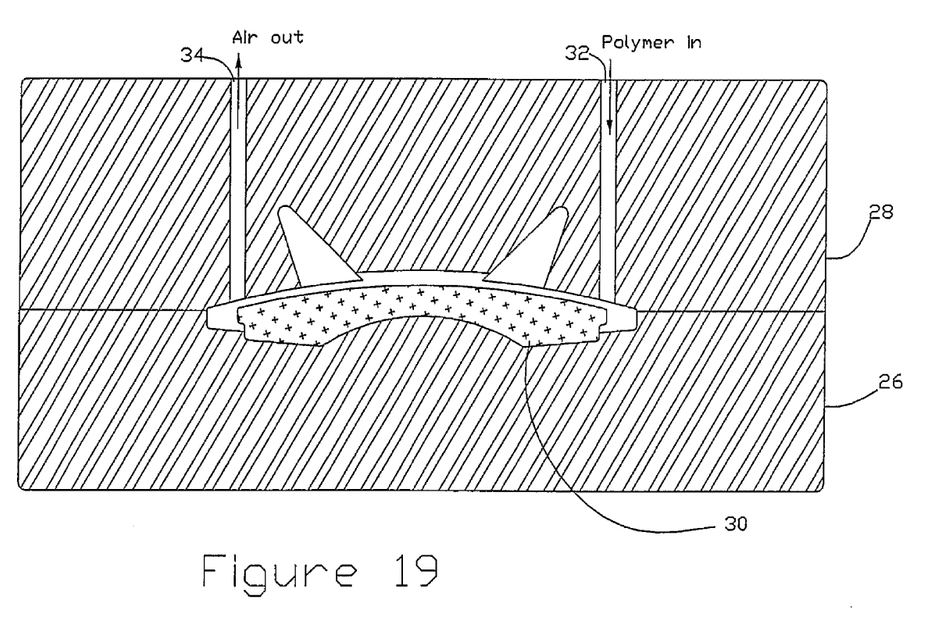
FIG. 19 is a cross-sectional view of a mold suitable for partially encapsulating the primary (articulating) material with the softer secondary (bone buttressing material) for one of the components of a motion restoring vertebral prosthesis of FIGS. 1-6.

FIG. 19 illustrates a simple two part injection mold comprising parts 26 and 28 with a first or articulating surface forming section 30 (illustrated as ceramic) placed therein. The secondary material, e.g., polymer, such as PEEK or CFRPEEK, is forced in duct 32 while air escapes through duct 34. The result is a finished or semi-finished component with the secondary material partially encapsulating the primary material. The upper exposed (and perhaps all of the) surface of the upper section may then be roughened and coated with a thin micron layer of Ti, etc. as desired.

Figure 20:
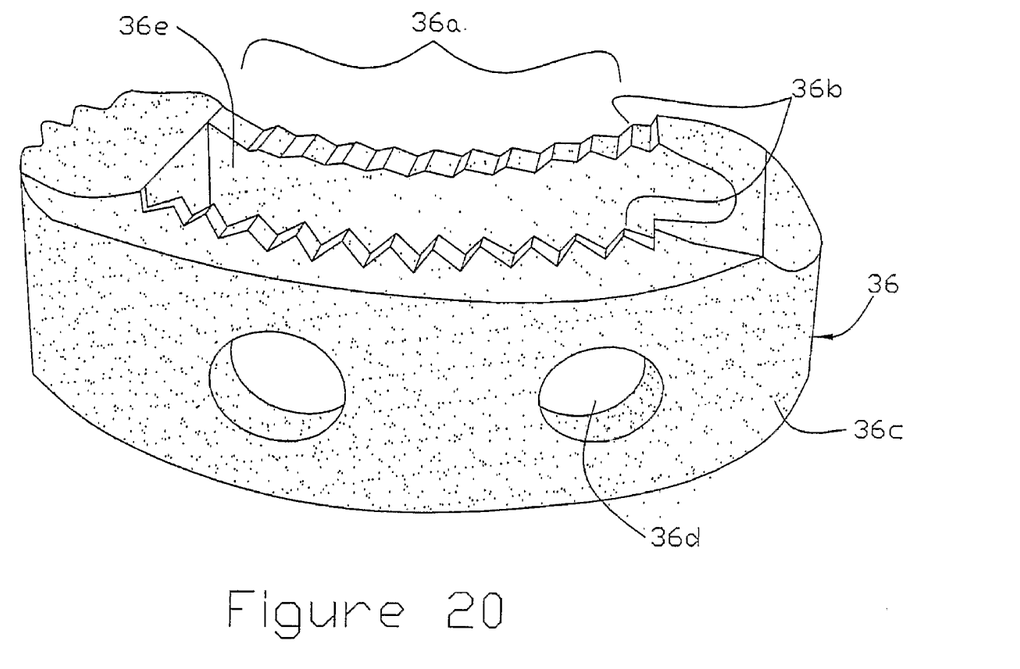
FIG. 20 is a perspective view of an artificial intervertebral spacer formed of a material, e.g., PEEK, and coated with a bone-on growth friendly material, e.g., Ti, for accommodating relatively uniform stress transfer to the vertebral bone faces while promoting bone-on growth attachment.

FIG. 20 illustrates a artificial intervertebral spacer 36 for placement in the space between adjacent vertebral bodies which has been vacated by a failed natural disc. The spacer is made of a relatively soft material, e.g., PEEK or CFRPEEK, having a flexural modulus similar to that of the bone forming the vertebral bodies to be fused.

The GPa flexural modulus of the soft material, as discussed previously, preferably is within the range of about 4-30 and most preferably about 17±8. The top bone buttressing surface 36 is formed with serrated edges or teeth 36b (i.e., providing an uneven surface). The spacer is roughened by an apparent blast media or tumbled in an abrasive media to create a micro surface roughening.

The spacer is then coated with a thin micron layer (i.e., 0.5 to 3-10 microns) of a material e.g., Ti, calcium phosphate or hydroxyaptite, which will promote bone-on growth without materially modifying the stress transfer characteristic between the soft material and the bone. The spacer is formed with holes 36d in the side walls and open central portion 36e as shown. The bottom bone buttressing surface (not shown) will be similar or identical to the top surface.

There has been described a novel prosthesis for restoring motion in an appendage or spinal joint which employs a relatively hard-stiff material to form the articulating surfaces while employing a softer less stiff material to form one or both bone buttressing surfaces to inhibit wear at the articulating surfaces while reducing stress shielding at the prosthesis bone interface(s). Preferably the softer material is provided with a thin micron coating of a material which promotes bone attachment without adversely affecting the reduction in stress shield. Additionally, there has been described a novel intervertebral spacer member having the flexural modulus comparable to that of the separated vertebrae while promoting bone attachment to the spacer member. Various modifications to the disclosed invention and perhaps improvements may and probably will occur to those skilled in the art without departing from the spirit and scope of our invention as defined in the appended claims.

The invention claimed is:

1. A motion restoring prosthesis to be interposed between the ends of mammalian bones adjoining a natural appendage or spinal joint to provide articulation therebetween comprising:

two components, each component defining an outer surface for attachment to a respect bone end and an articulating surface for engaging the articulating surface of the other component;

at least one of the components having an inner and outer section, the inner section defining the articulating surface and being formed of a primary, relatively hard, stiff material having a first flexural modulus, the outer section defining a bone facing surface to be attached to one of the bone ends and formed of a secondary softer material having a second flexural modulus, the first flexural modulus being greater than the second flexural modulus, the outer section functioning as a stress softening material to more evenly distribute the forces from the articulating surfaces to the associated bone end, wherein the bone facing surface of said at least one component has been roughened and/or made uneven to enhance an attachment of adjacent bone and covered with a thin coating of Ti within a range of 0.5 to 15 microns in thickness to enable bone-on growth while maintaining an appropriate distribution of forces through the thin coating of Ti to permit the stress shielding characteristic of the coated secondary softer material to be operative.

2. The motion restoring prosthesis of claim 1 wherein the first flexural modulus is about 70 or greater on the GPa scale and the second flexural modulus is about 60 or less on the GPa scale.

3. The motion restoring prosthesis of claim 1 wherein the secondary material is PEEK with or without the presence of carbon fiber reinforcement.

4. The motion restoring prosthesis of claim 1 wherein the other component also includes an inner section which corresponds in structure to the inner and outer sections of said at least one component.

5. The motion restoring prosthesis of claim 4 wherein the primary and secondary materials have a flexural modulus on the GPa scale of about 80 or more and 60 or less, respectively.

6. The motion restoring prosthesis of claim 5 wherein the prosthesis is an artificial spinal disc with the bone facing surfaces being generally planar to buttress respective vertebral bodies.

7. The motion restoring prosthesis of claim 1 wherein the secondary material has a flexural modulus on the GPa scale within the range of about 4-25.

8. The motion restoring prosthesis of claim 1 wherein the secondary material partially encapsulates the primary material to substantially prevent macromotion between the inner and outer sections of the components.

9. The motion restoring prosthesis of claim 8 wherein the secondary material is partially encapsulated around the primary material by an injection molding process.

10. The motion restoring prosthesis of claim 1 wherein the coating of Ti is within a range of 0.5 to 3.0 microns.

11. The motion restoring prosthesis of claim 10 wherein the bone facing surface has a micro surface roughening.

12. A motion restoring prosthesis or intervertebral spacer including a bone buttressing material having a GPa flexural modulus of about 60 or less and defining a bone buttressing surface, the bone buttressing surface functioning as a stress softening material, said surface being roughened or made uneven when abutted against the bone, to enhance an attachment of adjacent bone and covered with a thin coating of Ti within a range of 0.5 to 15 microns in thickness to enable bone-on growth while maintaining an appropriate distribution of force through the thin coating of Ti to permit the stress shielding characteristics of the bone buttressing surface to be operative.

13. The invention of claim 12 wherein the bone buttressing material is made of PEEK or CRFPEEK with a GPa flexural modulus within the range of about 4-30.

14. The invention of claim 13 wherein the GPa flexural modulus of the bone buttressing material is about 17±5-8.

15. The invention of claim 12 wherein the bone facing surface has a micro surface roughening.

16. The invention of claim 15 wherein the bone facing surface has a micro surface roughening.

17. An intervertebral spacer for replacing a natural disc, the spacer being formed of a material which has a GPa flexural modulus within the range of about 4-40 and defining opposing bone buttressing surfaces which are roughened or made uneven to enhance an attachment of adjacent bone and coated with a thin micron coating of a titanium bone-on growth enhancing material within a range of 0.5 to 15 microns in thickness which does not adversely affect bone stress transfer characteristics of the bone buttressing material.

18. The invention of claim 17 wherein the spacer material comprises PEEK or CRFPEEK with a GPa flexural modulus of about 17±5-8.

19. The invention of claim 17 wherein the bone facing surface has a micro surface roughening.

20. The invention of claim 19 wherein the bone facing surface has a micro surface roughening.

* * * * *